United States Patent [19]

Malamud et al.

[11] Patent Number: 4,788,707

[45] Date of Patent: Nov. 29, 1988

[54] RADIATION EXPOSURE GAUGE

[76] Inventors: Herbert Malamud, 30 Wedgewood Dr., Westbury, N.Y. 11590; Alex Chomenko, 3333 Henry Hudson Pkwy., Bronx, N.Y. 10463

[21] Appl. No.: 936,789

[22] Filed: Dec. 2, 1986

[51] Int. Cl.$^4$ .................... G01T 1/16; G01N 23/02; H05G 1/26
[52] U.S. Cl. .................... 378/207; 378/18; 378/162; 378/168
[58] Field of Search ............. 378/207, 62, 156, 158, 378/168, 165, 18, 162; 264/277

[56] References Cited

U.S. PATENT DOCUMENTS

| | | | |
|---|---|---|---|
| 1,953,249 | 4/1934 | Michel | 378/162 |
| 2,258,593 | 10/1941 | Black | 378/207 |
| 2,426,884 | 9/1947 | Kieffer | 378/162 |
| 4,550,422 | 10/1985 | Vanpelt | 378/207 |

FOREIGN PATENT DOCUMENTS 397825  9/1973  U.S.S.R. .................... 378/207

OTHER PUBLICATIONS

Lin, P. P., "Penetration Quality Measurement for Standardization of Radiographic Image Quality," *Medical Physics*, vol. 2, No. 1, Jan./Feb. 1975, pp. 5–8.

"Textbook of Dental Radiography", Langland et al., pp. 191 and 193 (Charles C. Thomas, 1973).

Copy of a Trouble Shooting Guide for Dental Radiographic Normalizing & Monitoring Device, copyrighted by Perrygraf/Slide Chart Corp., 1985.

*Primary Examiner*—Craig E. Church
*Assistant Examiner*—T. N. Grigsby
*Attorney, Agent, or Firm*—Ronni S. Malamud; Alvin Browdy; Sheridan Neimark

[57] ABSTRACT

The present invention relates to a gauge for use with x-ray machines to calibrate correct technic values (exposure, kilovoltage, processing conditions, etc.) for x-ray film to yield anatomically correct film densities over the visible density range. The gauge accomplishes this by including only four sections. In particular, a first portion for achieving correct film densities at the low end of the visible density range and a second portion for achieving correct film densities at the high end of the visible density range. The gauge also includes at least one region for achieving a slight variation in film density in each of the first and second above-named portions. The gauge may be encased by being cast in plastic of a particular thickness and absorption of x-rays. With this gauge, the radiographer examines film densities at the upper and lower limits of the visible density range to distinguish overexposure, upper limits of correct exposure, correct exposure, lower limit of correct exposure and underexposure.

16 Claims, 2 Drawing Sheets

RADIATION EXPOSURE GAUGE

BACKGROUND OF THE INVENTION

1. Field of the Invention

The present invention relates to a gauge for determining, adjusting, and checking radiographic exposures, that will aid radiographers in producing x-ray films which are correctly exposed at various machine settings of voltage, current, and exposure time, and for various films, grids, screens and other accessories affecting exposure, or any other factors that effect exposure.

2. The Prior Art

For purposes of describing the device according to the present invention, we shall describe a phantom, or gauge, developed specifically for dental use. It is understood, however, that the gauge may be adapted for use with other parts of the body.

Much attention in recent years has been given to reducing the amount of x-rays dental patients receive during routine checkups. One way of reducing the amount of x-rays is to provide for the taking of better x-ray pictures, thus reducing the need for re-takes. In order to accomplish this goal, the x-ray machine must be calibrated frequently to ensure proper exposure in spite of possible drifting in supply voltage to the machine, or aging and temperature variations of the film developer.

The prior art tools that were developed depended on the judgement of the dentist to determine whether the film was correctly exposed.

Heretofore, patients, skeletal phantoms and step wedges had been used for testing film exposure. Using patients to test exposure has two major disadvantages, the first being that time consuming evaluation of anatomic detail is required and the second being that unnecessary patient exposure to potentially harmful x-rays is required. The skeletal phantoms also require time consuming evaluation of anatomic detail and the phantoms are costly.

The film step wedge is one type of prior art device used as a standard for the dentist to compare with his film.

The device includes a piece of thin metal having just the right thickness so that a film exposed through it correctly (x-ray voltage, current and time, as well as film speed and same position relative to the machine as the patient's tooth) would have exactly the same density as the center step of the film step wedge. If the density obtained were the same as either step of the film wedge next to the center, the dental film exposed that way would be a bit too dark (or too light) but still usable. If it matched the steps further from the center, towards either end of the film wedge, the film would be too dark or too light to be useful clinically.

However, this prior art film step wedge, which was made on gray base film, does not work adequately on all brands of film. Each brand comes with variations to suit each user's taste. One such variation is the color of the plastic base on which the emulsion is put. A film wedge made on gray base film can not be used to test blue base film because the densities can not be easily compared by eye. Even with the same density, the films will look different.

The step wedge provides a number of other disadvantages. When visual comparisons are made, the amount of correction cannot easily be established. Further, a correctly exposed reference film is required. Finally, there is no way to distinguish between the upper limit of correct exposure and overexposure and between the lower limit of correct exposure and underexposure.

Densitometric comparison of the step wedge films removes the subjective judgement but still requires a correctly exposed reference film and the densitometer is a costly piece of equipment.

Thus a different tool was developed which included a brass step wedge. This has five brass steps, of thickness 0.004, 0.006, 0.008, 0.010 and 0.012 inch. Additionally, in another spot, a sheet of brass 0.008 of an inch thick is included. The user, when the x-ray machine is in perfect operating adjustment, and has fresh developer, etc., (such as when a repairman has placed it in good working order) exposes a film on the wedge side of the phantom, or tool and develops it. He inserts the film into a slot in the phantom, and leaves it there. When he wants to check working conditions, he exposes another film through the 0.008 inch brass plate side of the phantom and compares it with the wedge. If he decides to change to a different film, he makes another film wedge.

Both of these prior art phantoms may not be accurate or consistent in the results achieved because they depend on the subjective judgement of the dentist to determine whether the exposure is as it should be.

An "X-ray Checker", another type of prior art phantom, is described in the *Textbook of Dental Radiography*, by O. E. Langland and F. H. Sippy (Illinois: Charles C. Thomas 1973) at pages 191–193. However, the disadvantages discussed with respect to the step wedge likewise occur with the "X-ray Checker".

SUMMARY OF THE INVENTION

It is an object of this embodiment of the invention to provide a dental x-ray phantom, or gauge, which is accurate and consistent in the results produced and does not depend on the subjective judgement of the dentist.

It is a further object of the invention to provide a tool which can be used to check whether an x-ray unit is being used at the correct exposure and to check whether the x-ray unit is in compliance with NCDRH guidelines on patient exposure.

It is a further object of the present invention to provide a gauge the use of which will allow instant film analysis.

It is a further object of the present invention to provide a gauge which is less costly than the skeletal phantom and more objective than step wedge densitometry.

It is a further object of the present invention to provide a gauge which is more accurate than the step wedge.

It is a further object of the present invention to provide a gauge which accurately distinguishes all five film density conditions: overexposure, upper limit of correct exposure, correct exposure, lower limit of correct exposure, and underexposure. Overexposure occurs when there is too much radiation, causing loss of high density detail. The upper limit of correct exposure is the maximum permissible exposure level for viewing anatomic detail, where greater levels will cause loss of high density detail. Correct exposure is that optimum exposure which yields a density in the range where even slight density variations are visible. The lower limit of correct exposure is the minimum permissible exposure level for viewing anatomic detail, where lesser levels will cause loss of low density detail. Underexposure occurs when there is not enough radiation, causing loss of low density detail.

Further objects and advantages of the invention will become apparent from a consideration of the drawings and ensuing description thereof.

According to one aspect of the present invention, a gauge is provided for use with x-ray machines to calibrate correct exposure values for x-ray film to yield film densities in a visible density range. The gage includes first means for achieving film densities at a low end of the visible density range, second means for achieving film densities at a high end of the visible density range, and means for achieving a slight variation in film density in each of the first and second means.

The means for achieving a slight variation includes at least one region associated with each of the first means and the second means for varying the film density between a portion of film exposed through each region and a portion of film exposed through the first means and the second means not exposed through each region. The first means comprises a first layer which extends over at least a portion of the gauge an has a first predetermined thickness. The at least one region comprises a region of the first layer which has a second predetermined thickness, the second predetermined thickness being thinner than the first predetermined thickness. The at least one region includes a first region of the first layer having a second predetermined thickness and a first plate obscuring a first portion of the second means, and a second region of the first layer having a third predetermined thickness and a second plate obscuring a second portion of the second means. The first region and the first plate define a range of film densities under ideal exposure values. The second region and the second plate define a range of film densities under usable exposure values and the second and third predetermined thicknesses are thinner than the first predetermined thickness.

According to another aspect of the present invention a phantom for use with x-ray machines is provided to calibrate exposure values for x-ray film. The phantom includes a first layer which covers a first side of the phantom and plate means positioned in a second plane and located on a second side of the phantom which does not contain the first layer. The first layer has a first predetermined thickness and extends across approximately one-half of the area of the phantom in a first plane. The first layer includes a first region which has a second predetermined thickness, the second predetermined thickness being thinner than the first predetermined thickness.

The phantom may include cutout means for receiving the x-ray film.

The first layer comprises a lead plate. The lead plate is approximately 0.040 of an inch thick.

The phantom comprises a phantom body constructed of plastic. The phantom body has a width and length approximately one-half of an inch larger than the width and length of the x-ray film and has a thickness of approximately one-half of an inch. The phantom body may include a backing plate hingedly connected to one edge of a rear portion of the phantom body. The backing plate is made of lead and is approximately one-sixteenth of an inch thick.

The first region may be circular in shape and may have a diameter of approximately 1 cm. The first region may be in the shape of a line which has dimensions of approximately 5 mm by 10 mm. The first region only partially covers the first side of the phantom and may be 0.016 of an inch thick.

The plate means is made of aluminum. The plate means may be circular in shape and have a diameter of approximately 1 cm. The plate means may be in the shape of a line which has dimensions of approximately 5 mm by 10 mm. The plate means only partially covers the second side of the phantom and may be 0.004 of an inch thick.

The first region includes a second region having a first predetermined thickness and a third region having a second predetermined thickness, wherein the second region defines a range of film densities under ideal exposure values and the third region defines a range of film densities under usable exposure values. The plate means includes a first plate having a third predetermined thickness and a second plate having a fourth predetermined thickness, wherein the first plate further defines the range of film densities under ideal exposure values and the second plate further defines the range of film densities under usable exposure values.

BRIEF DESCRIPTION OF THE DRAWINGS

The invention of the present application will now be described in more detail with reference to the preferred embodiments of the device, given only by way of example, and with reference to the accompanying drawings, in which.

DETAILED DESCRIPTION OF THE PREFERRED EMBODIMENT

Figure 1:
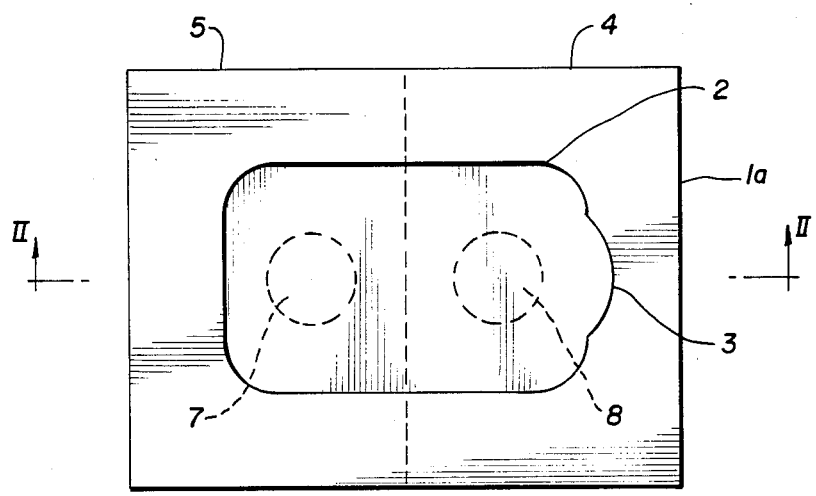
FIG. 1 is a plan view of the gauge according to one embodiment of the present invention.

Reference should be made to the drawing where like reference numerals refer to like parts.

FIG. 1 is a front plan view of the dental gauge or phantom 1 according to the first embodiment of the present invention. Gauge 1 includes phantom body 1a which is constructed of plastic and is approximately one-half inch thick. The plastic, or any other material appropriate for a phantom, should be made such that exposure of a dental film with the correct exposure values, yields a density of approximately 2.0. A density of approximately 2.0 is chosen because, under viewing conditions usual to a dental office, it is the maximum density at which slight density variations (about 3%) are still visible. A density of approximately 2.0 appears just lighter than black, and represents the upper limit of the visible density range. The visible density range is that in which, under optimum viewing conditions, the human eye can perceive a wide scale of grays between completely white and completely black.

Figure 2:
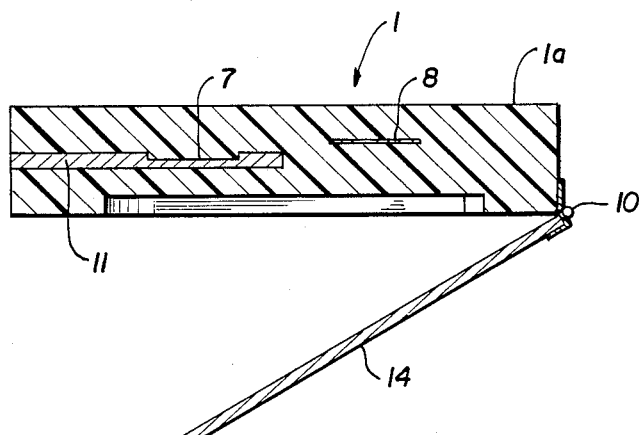
FIG. 2 is a cross-sectional view of the gauge according to the embodiment of the present invention shown in FIG. 1 taken along the line 11—11 in FIG. 1.

A cross-sectional view of the embodiment shown in FIG. 1, along the line A—A is shown in FIG. 2.

Gauge 1 includes film cutout 2 which has dimensions approximately equal to the size of the x-ray film packet (not shown) to be used. Notch 3 is provided at one side of film cutout 2 to enable fingernail access to the film packet. The outer dimensions of gauge 1 should be approximately one-half of an inch larger than film cutout 2 at each side.

Gauge 1 is divided into two sides 4 and 5, each of which covers one-half of the area of the gauge. Embedded in side 5 is lead plate 11 disposed in one plane of gauge 1. Lead plate 11 is approximately 0.040 of an inch (1mm) thick and is constructed such that a density of about 0.25 is obtained when x-ray film is exposed through lead plate 11 when the correct exposure values are used. At a density of approximately 0.25, slight variations (about 3%) are still visible under viewing conditions usual in a dental office. A density of approximately 0.25 appears just darker than white and represents the lower limit of the visible density range.

Side 4 is partially obscured by the addition of a patch or layer of material. The additional material may be in the shape of a circle, such as circle 8 with a diameter of approximately 1 cm, a line having dimensions of approximately 5 mm by 10 mm, or any other shape or pattern. In the first embodiment shown in the drawings, lead plate 11 includes a region, shown at circle 7 in the drawings, which has a reduced thickness with respect to the remainder of plate 11. In this region, the lead is 0.016 of an inch (0.4 mm) thick. On side 4, circle 8 is made of aluminum, 0.004 of an inch (0.1 mm) thick. Lead plate 11 forms the first means for achieving a film density at the low end of the visible density range in a first film region. Body 1a forms the second means for achieving a film density at the high end of the visible density range in a second film region. Circle 7 forms the third means for achieving a film density in a third film region slightly higher than the density in the first film region while circle 8 forms the fourth means for achieving a film density in a fourth film region slightly lower than the density in the second film region.

The functions of each of the above identified parts of the gauge are summarized in Table I below.

TABLE I

| Part | Function |
| --- | --- |
| High density area | |
| (A) Dot | Simulates upper limit of visible density |
| (B) Background | Simulates above upper limit |
| Low density area | |
| (C) Dot | Simulates lower limit of visible density |
| (D) Background | Simulates below lower limit |

With overexposure A becomes B and difference is obscured.
With underexposure C becomes D and difference is obscured.

Gauge 1 includes backing plate 14 which is approximately one-sixteenth of an inch thick and is made of lead. Backing plate 14 is attached to body 1a of gauge 1 by hinge 10, by which backing plate 14 is opened to insert the x-ray film into gauge 1. Backing plate 14, being lead, absorbs the x-rays that pass through the film when the phantom is exposed by the x-ray machine, preventing their being scattered back and reducing the image contrast.

According to the principle of operation of the present invention, the phantom, or gauge, simulates anatomic x-ray absorbtion of a specific anatomic region, e.g. dental arch, skull, chest, foot, etc. With correct exposure, two dots, or spots, are visualized. The "dot" in the low density area (the light area on the film), appearing just darker than white, represents the anatomic structure with the greatest x-ray absorptions. The "dot" in the high density area (the dark area on the film), appearing just lighter than black, represents the anatomic structure with the least x-ray absorption. Overexposure of the film obsures the "dot" in the high density area. Underexposure obscures the "dot" in the low density area.

The gauge is used as follows. An intraoral film is inserted via backing plate 14 into film cutout 2. Alternatively, the gauge is placed on a film packet, or on a cassette containing film/screens. The x-ray machine is set with the desired exposure values. The gauge is photographed by the x-ray machine as if it were an actual patient, at the same distance from the x-ray machine that a patient would be located. The film is then processed as recommended by the film manufacturer. The finished film should be viewed using optimum viewing conditions, that is, using standard viewbox illumination, masking extraneous viewbox light and reducing room light.

A film exposed through this phantom shows a dark half and a light half, and on each, a very slightly lighter or darker spot, in the shape of, for example, a circle, which is just barely visible. The spot corresponds to the shape used for the regions, that is, circles 7 or 8 discussed above. Normally, when the exposure time is 50% more, the dental film would be darker, but still barely usable. With the gauge according to the present invention, the clear, or lighter side of the film, that is the side of the film exposed through side 5 which includes lead plate 11, is darker and the spot is more easily visible. The dark side of the film which is exposed through side 4, is so dark that the spot image could not be seen.

Conversely, when the exposure time is set at one-half the correct time, the spot on the light side of the film would become invisible and the spot on the dark side would be more easily visible.

Changes in voltage, current or development produce an effect similar to that of changes in exposure time. That is, they change the density of all parts of the film in either the darker or the lighter direction.

These results are summarized and compared with the films obtained with a skeletal phantom in Table II below. The densitometry of the films obtained using the gauge according to the present invention appears in Table III.

TABLE II

| | Film finding* | | |
| --- | --- | --- | --- |
| Film exposure** | Gauge High density area "Dot" Visibility | Low density area "Dot" Visibility | Skeletal Anatomic detail Visibility |
| 3 times correct | No | Yes | No detail |
| 2 times correct | No | Yes | High density detail lost |
| 1.5 times correct | Slight | Yes | Dark but visible detail |
| Correct | Yes | Yes | All detail visible |
| .75 correct | Yes | Slight | Light but visible detail |
| .50 correct | Yes | No | Low density detail lost |
| .25 correct | Yes | No | No detail |

*E speed film
**Based on film manufacturer's recommended processing, and optimum viewing condition

TABLE III

| | Measured densities | | | | |
| --- | --- | --- | --- | --- | --- |
| | High density area "Dot" | | | Low density area "Dot" Background %* | |
| Film exposure | Background %* | | | | |
| 3 times correct | No | 3.33 | | .33 | .22 | 33.3 |
| 2 times correct | No | 3.00 | | .27 | .22 | 18.5 |
| 1.5 times | 2.47 | 2.54 | 2.76 | .25 | .21 | 16.0 |

TABLE III-continued

| Film exposure | High density area "Dot" | Background | %* | Low density area "Dot" | Background | %* |
|---|---|---|---|---|---|---|
| correct |  |  |  |  |  |  |
| Correct | 2.09 | 2.19 | 4.57 | .23 | .20 | 13.0 |
| .75 correct | 1.78 | 1.90 | 6.32 | .21 | .19 | 9.5 |
| .50 correct | 1.28 | 1.32 | 3.03 | No | .19 |  |
| .25 correct | .54 | .57 | 5.26 | No | .18 |  |

*Contrast

The phantom is repeatedly exposed to the x-rays and each time a test film is made, until the correct exposure values are determined such that the spots on both sides of the phantom are visible.

Table IV below is a representation of the results one can obtain using the gauge according to the above techniques.

TABLE IV

| Film Finding | | |
|---|---|---|
| High density area "Dot" visibility | Low density area "Dot" visibility | Exposure Condition |
| No | Yes | overexposed |
| Slight | Yes | upper limit of correct exposure |
| Yes | Yes | correct exposure |
| Yes | Slight | lower limit of correct exposure |
| Yes | No | underexposed |

Figure 3:
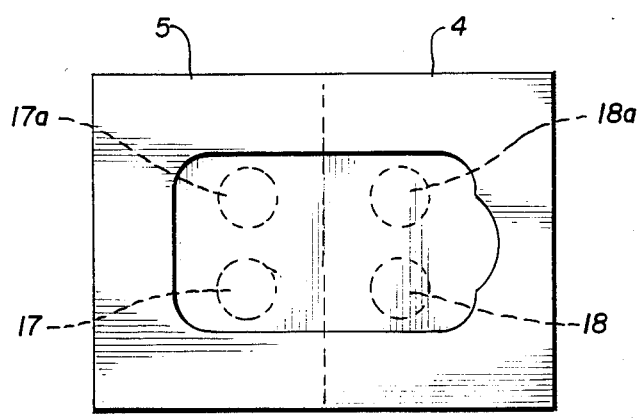
FIG. 3 is a plan view of the gauge according to a second embodiment of the present invention.

The thickness of the metal layers determines the latitude of densities shown as acceptable by use of the phantom. Thus, if smaller thickness difference between plates and dot are used, their image is extinguished on the test film with narrower exposure latitude. The second embodiment of the gauge, shown in FIG. 3, has two regions 17 and 17a of lead plate 11, each having different thicknesses and each being thinner than the thickness of lead plate 11. Two metal plates 18 and 18a having different thicknesses are associated with side 4 and may be disposed in a different plane than lead plate 11 within gauge 1. Viewing the image produced on the film by region 17 and plate 18, for example, would define the range of densities under ideal exposure. Region 17a and plate 18a, for example, would define a poorer, but still usable range of film densities under slightly less than ideal exposure. If both images on one side of the phantom test film were not visible, the exposure is too far from ideal to be clinically acceptable.

The gauge according to the present invention, without any design modifications, will operate effectively for any film, with or without screens, guides, etc., at any range or with any collimator. The only requirement is that the film being exposed should be at the position of the patient, so that phantom exposure is the same as the patient exposure.

The phantom is also useful for checking whether an x-ray unit is being used correctly, such as to check compliance with NCDRH guidelines. The accuracy and range of this check can be controlled by varying the thickness of the added metal plates.

The same design can also be used for medical x-ray exposure for any part of the body. A separate phantom would be made for each part of the body.

Thus, as mentioned briefly above, the phantom may have, instead of a region of increased x-ray absorption and a region of decreased absorption, two regions of increased absorption, created by adding a layer which partially obscures lead plate 11 and reducing the thickness of lead plate 11 to a maximum of approximately 0.016 of an inch. Alternatively, two regions of decreased absorption can be created by using the reduced thickness region of lead plate 11 described above, and hollowing out part of the plastic body in the other section of the phantom instead of inserting plate 8. The operation of this variation of the invention is the same as the operation of the first embodiment.

It is to be understood that the above detailed description of the various embodiments of the invention is provided by way of example only. Other details of design and construction may also be modified without departing from the true spirit and scope of the invention as set forth in the appended claims.

What is claimed is:

1. A gauge for use with x-ray machines to distinguish the following five x-ray film conditions, overexposure, upper limit of correct exposure, correct exposure, lower limit of correct exposure, and underexposure, by examining film densities at the upper and lower limits of the visible density range, consisting only of:
   a. first means for achieving a film density at the low end of the visible density range in a first film region;
   b. second means for achieving a film density at the high end of the visible density range in a second film region;
   c. third means for achieving a film density, in a third film region, slightly higher than the low end of the visible density range, said third region being contiguous with the first film region;
   d. fourth means for achieving a film density, in a fourth film region, slightly lower than the high end of the visible density range, said fourth region being contiguous with the second film region,
   such that the degree of visibility of the difference between the film densities in said first and third regions and the degree of visibility of the difference between the film densities in said second and fourth regions indicates the correctness of the exposure of the x-ray film.

2. The gauge according to claim 1 wherein said first means comprises a first layer extending over at least a portion of said gauge, said first layer having a first predetermined x-ray absorption.

3. The gauge according to claim 2 wherein said first means comprises a first layer of lead approximately 0.040 of an inch thick.

4. The gauge according to claim 2 wherein said second means comprises a second layer extending over at least a poriton of said gauge, said second layer having a second predetermined x-ray absorption.

5. The gauge according to claim 4 wherein said third means comprises a third layer contiguous with said first layer and having a third predetermined x-ray absorption, said third predetermined x-ray absorption being sufficient to produce a 3% density difference from the density of the first film region.

6. The gauge according to claim 5 wherein the first layer covers approxiamtely one half the area of a dental x-ray film, and the third layer comprises a circular thinner portion of said first layer of lead, said portion being approximately 1 centimeter in diameter.

7. The gauge according to claim 5 wherein said third means comprises a third layer composed of lead approximately 0.016 of an inch thick.

8. The gauge according to claim 7 wherein the first, third and fourth layers are embedded in the body of the gauge.

9. The gauge according to claim 5 wherein said fourth means comprises a fourth layer extending over a region of the gauge contiguous with said second layer and having a fourth predetermined x-ray absorption, said fourth predetermined x-ray absorption being sufficient to produce a 3% density difference from the density of the second film region.

10. The gauge according to claim 9 wherein said fourth means comprises a fourth layer, composed of aluminum approximately 0.004 of an inch thick.

11. A gauge according to claim 10 wherein the fourth layer of aluminum is a disk approximately 1 centimeter in diameter.

12. The gauge according to claim 9 wherein said second means comprises a body of the gauge, said body being composed of a cast plastic approximately 0.5 of an inch thick.

13. The gauge according to claim 12 wherein said body has a width and length approximately one-half of an inch larger than the width and length of said x-ray film.

14. The gauge according to claim 12 wherein said body comprises a backing plate hingedly connected to one edge of a rear portion of said body.

15. The gauge according to claim 14 wherein said backing plate is made of lead.

16. The gauge according to claim 14 wherein said backing plate is approximately one-sixteenth of an inch thick.

* * * * *